(12) United States Patent
Kim et al.

(10) Patent No.: US 11,779,896 B2
(45) Date of Patent: Oct. 10, 2023

(54) MAGNETIC-OPTICAL COMPOSITE NANOSTRUCTURE

(71) Applicant: KOREA UNIVERSITY RESEARCH AND BUSINESS FOUNDATION, Seoul (KR)

(72) Inventors: Young Keun Kim, Seoul (KR); Yu Jin Kim, Seongnam-si (KR); Bum Chul Park, Seoul (KR); Myeong Soo Kim, Suwon-si (KR)

(73) Assignee: Korea University Research and Business Foundation, Seoul (KR)

( * ) Notice: Subject to any disclaimer, the term of this patent is extended or adjusted under 35 U.S.C. 154(b) by 449 days.

(21) Appl. No.: 16/987,816

(22) Filed: Aug. 7, 2020

(65) Prior Publication Data
US 2021/0046443 A1 Feb. 18, 2021

(30) Foreign Application Priority Data
Aug. 13, 2019 (KR) .................. 10-2019-0098793

(51) Int. Cl.
| | |
|---|---|
| *B01J 13/02* | (2006.01) |
| *B03C 1/30* | (2006.01) |
| *G01N 33/543* | (2006.01) |
| *G01N 33/553* | (2006.01) |
| *B82Y 40/00* | (2011.01) |
| *B82Y 15/00* | (2011.01) |
| *B82Y 35/00* | (2011.01) |

(52) U.S. Cl.
CPC .............. *B01J 13/02* (2013.01); *B03C 1/30* (2013.01); *G01N 33/54326* (2013.01); *G01N 33/54346* (2013.01); *G01N 33/54353* (2013.01); *G01N 33/553* (2013.01); *B82Y 15/00* (2013.01); *B82Y 35/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 2011/0275061 A1* | 11/2011 | Weidemaier ..... | G01N 33/54333 977/773 |
| 2015/0118688 A1* | 4/2015 | Weidemaier ........... | C12M 33/04 422/522 |

FOREIGN PATENT DOCUMENTS

| | | |
|---|---|---|
| CN | 102728385 A | 10/2012 |
| CN | 102812348 A | 12/2012 |
| CN | 106404747 A | 2/2017 |
| KR | 10-2009-0030775 | 3/2009 |
| KR | 10-2012-0116277 A | 10/2012 |

OTHER PUBLICATIONS

Chinese Office Action dated Nov. 2, 2022, in counterpart Chinese Patent Application No. 202010806468.5 (9 pages in Chinese).
Khlebtsov, Boris, et al., "Surface-enhanced Raman scattering inside Au@Ag core/shell nanorods," *Nano Research*, 9, 8, 2016 (pp. 2303-2318).
Korean Office Action dated Nov. 26, 2020 in counterpart Korean Patent Application No. 10-2019-0098793 (4 pages in Korean).

* cited by examiner

*Primary Examiner* — Jeffrey D Washville
(74) *Attorney, Agent, or Firm* — NSIP Law

(57) ABSTRACT

The present invention relates to a magnetic-optical composite nanostructure, which has a heterogeneous nature due to consisting of a first core-shell nanoparticle and second core-shell nanoparticles and thus realizes magnetic and optical functions at the same time.

12 Claims, 10 Drawing Sheets

MAGNETIC-OPTICAL COMPOSITE NANOSTRUCTURE

CROSS-REFERENCE TO RELATED APPLICATION

This application claims priority to and the benefit of Korean Patent Application No. 10-2019-0098793, filed on Aug. 13, 2019, the disclosure of which is incorporated herein by reference in its entirety.

BACKGROUND

1. Field of the Invention

The present invention relates to a magnetic-optical composite nanostructure, and more particularly, to a magnetic-optical composite nanostructure which has a heterogeneous nature due to consisting of a first core-shell nanoparticle and second core-shell nanoparticles and thus realizes magnetic and optical functions at the same time.

2. Discussion of Related Art

Conventionally, as in-vitro diagnostic biomolecule detection methods, an enzyme-linked immunosorbent assay (ELISA), flow cytometry, and the like have been used. However, since such analysis methods are carried out using kits and equipment imported from overseas, the methods are expensive and time-consuming. In addition, organic phosphors have a short lifetime and are highly likely to cause inspection errors due to having poor stability.

In order to solve the above-described problems, recently, nanomaterials having high detection sensitivity are used in various ways. Among these, biomolecule or biomaterial detection using a surface-enhanced Raman scattering (SERS) phenomenon has been applied using various types of gold and/or silver nanoparticles (Patent Document 1). However, since such a method does not have magnetic characteristics, it is not possible to separate only the molecule or protein to be captured.

Therefore, beads having magnetic characteristics have been used, but the method using the beads has a process that is rather complicated to extract specific molecules or proteins to be captured.

Meanwhile, in the case of the multifunctional nanoparticles suggested as an alternative, in which metals and metal oxides are combined, contrary to the expectation that the multifunctional nanoparticles will have very high applicability, it is difficult to uniformly realize magnetic and optical characteristics at the same time in a single nanoparticle, and therefore, the applicability of the nanoparticles is limited.

RELATED-ART DOCUMENT

Patent Document

1. Korean Laid-Open Patent Application No. 10-2009-0030775

SUMMARY OF THE INVENTION

The present invention is directed to providing various types of multifunctional magnetic-optical composite nanostructures, each of which includes a precious metal (gold and/or silver) capable of producing a SERS signal and a magnetic nanoparticle, a method of manufacturing the same, and cell imaging ability and biomolecule or biomaterial detection ability based on the use of the same.

One aspect of the present invention provides a method of manufacturing a magnetic-optical composite nanostructure, which includes: preparing a first core-shell nanoparticle by forming a ceramic shell on a magnetic nanoparticle; preparing a gold nanoparticle-attached core-shell nanoparticle by attaching gold nanoparticles to the first core-shell nanoparticle; primarily growing the gold nanoparticles of the gold nanoparticle-attached core-shell nanoparticle; preparing a Raman molecule-functionalized core-shell nanoparticle by functionalizing the primarily grown gold nanoparticles with a Raman molecule; and preparing second core-shell nanoparticles by forming a gold, silver, or gold-silver alloy shell on each of the Raman molecule-functionalized gold nanoparticles of the Raman molecule-functionalized core-shell nanoparticle.

Another aspect of the present invention provides a magnetic-optical composite nanostructure, which is manufactured by the above-described manufacturing method and includes: a first core-shell nanoparticle having a magnetic nanoparticle core and a silica shell; and second core-shell nanoparticles, each of which has a gold nanoparticle core and a gold, silver, or gold-silver alloy shell, wherein the second core-shell nanoparticle is bonded to a functional group formed on the surface of the shell of the first core-shell nanoparticle, and the gold nanoparticle core is functionalized with a Raman molecule.

Still another aspect of the present invention provides an analyte detection kit, a molecular diagnostic chip, or a diagnostic imaging composition including the above-described magnetic-optical composite nanostructure.

Yet another aspect of the present invention provides a method of detecting, imaging, or separating an analyte, which includes: functionalizing the surface of the above-described magnetic-optical composite nanostructure with a biomolecule capable of binding to an analyte to be detected; exposing the functionalized magnetic-optical composite nanostructure to a sample containing one or more analytes; and identifying an analyte bound to the magnetic-optical composite nanostructure using Raman spectroscopy.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
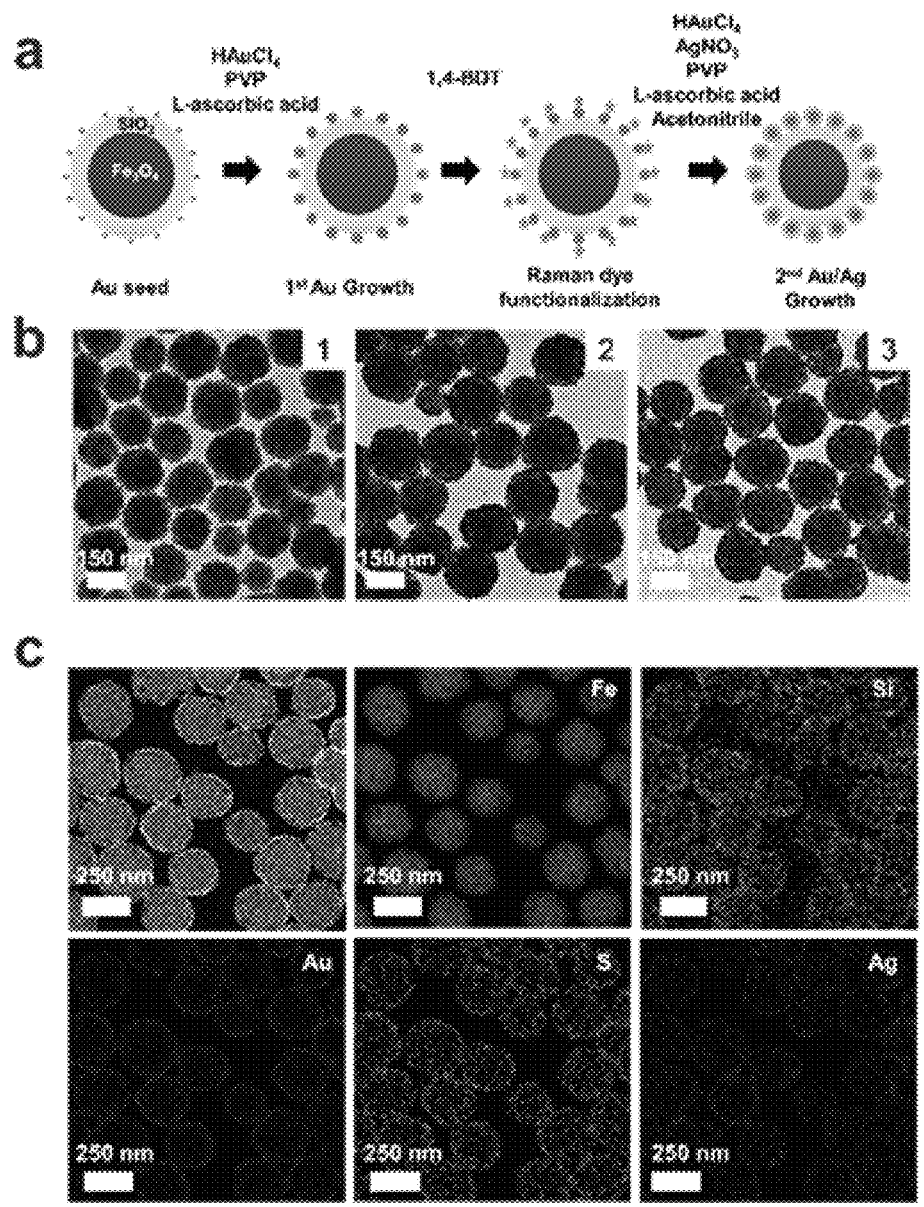
FIG. 1 is a set of images including (a) a schematic diagram illustrating a process of manufacturing a magnetic-optical composite nanostructure according to the present invention, (b) transmission electron microscope (TEM) images obtained in each step of the above schematic diagram, and (c) a TEM image and energy dispersive X-ray spectroscopy (EDX) images of S3.

Hereinafter, the present invention will be described in detail.

The present invention relates to a method of manufacturing a magnetic-optical composite nanostructure, which includes:

(A) preparing a first core-shell nanoparticle by forming a ceramic shell on a magnetic nanoparticle (hereinafter referred to as a first-core-shell nanoparticle preparation step);

(B) preparing a gold nanoparticle-attached core-shell nanoparticle by attaching gold nanoparticles to the first core-shell nanoparticle (hereinafter referred to as a gold nanoparticle-attached core-shell nanoparticle preparation step);

(C) primarily growing the gold nanoparticles of the gold nanoparticle-attached core-shell nanoparticle (hereinafter referred to as a primary growth step);

(D) preparing a Raman molecule-functionalized core-shell nanoparticle by functionalizing the primarily grown gold nanoparticles with a Raman molecule (hereinafter referred to as a Raman molecule-functionalized core-shell nanoparticle preparation step); and (E) preparing second core-shell nanoparticles by forming a gold, silver, or gold-silver alloy shell on each of the Raman molecule-functionalized gold nanoparticles of the Raman molecule-functionalized core-shell nanoparticle (hereinafter referred to as a secondary growth step).

According to the present invention, in the (A) first-core-shell nanoparticle preparation step, magnetic nanoparticle/ceramic core-shell nanoparticles are prepared by forming a ceramic shell on each of the magnetic nanoparticles.

This step may be carried out by adding a ceramic precursor solution to a first solution including the magnetic nanoparticles, and thereby a second solution including the first core-shell nanoparticles may be prepared.

In one embodiment, a magnetic nanoparticle may form the core of the first core-shell nanoparticle. The magnetic nanoparticle may be a metal oxide nanoparticle, and the metal oxide may be one or more selected from the group consisting of FeO, Fe$_2$O$_3$, Fe$_3$O$_4$, CoFe$_2$O$_4$, NiFe$_2$O$_4$, MnFe$_2$O$_4$, TiO$_2$, ZrO$_2$, CeO$_2$, Al$_2$O$_3$, and MgO. In the present invention, magnetic characteristics may be imparted to the finally obtained composite nanostructure by using the metal oxide.

The magnetic nanoparticle may consist of clusters of magnetic nanoparticles.

The average particle diameter of such magnetic nanoparticles or clusters is not limited as long as it is greater than that of the second core-shell nanoparticle to be described below, and may be, for example, in the range of 10 to 500 nm, 50 to 400 nm, or 100 to 200 nm. In addition, the magnetic nanoparticles or clusters may be spherical. In the present invention, the term "spherical" may be used to encompass not only the spheres mathematically defined as three-dimensional shapes consisting of points all at the same distance from one point, but also all seemingly round shapes.

In one embodiment, the ceramic shell may serve to protect the magnetic nanoparticle.

The ceramic may include one or more selected from the group consisting of silica, titania, zirconia, alumina, and zeolite, and in the present invention, silica may be used as the ceramic. When the silica is used, the shell may be referred to as a silica shell.

The thickness of such a shell is not particularly limited, and may be adjusted, for example, in the range of 1 to 100 nm or 1 to 20 nm.

In one embodiment, the ceramic shell may be formed through a reaction between the magnetic nanoparticle and the ceramic precursor. Here, as the ceramic precursor, an alkoxy compound may be used, and specifically, tetraethoxysilane (TEOS) may be used.

According to the present invention, in the (B) gold nanoparticle-attached core-shell nanoparticle preparation step, a gold nanoparticle-attached core-shell nanoparticle is prepared by attaching gold nanoparticles to the first core-shell nanoparticle.

This step may include introducing a functional group onto the surface of the shell of the first core-shell nanoparticles and allowing a gold nanoparticle seed to be bonded to the functional group.

Specifically, the step may be carried out by adding a compound having the functional group to the second solution prepared in the step (A), and thereby a third solution including magnetic nanoparticle/ceramic core-shell nanoparticles having a shell surface onto which the functional group has been introduced may be prepared. Further, by adding gold nanoparticles to the third solution, a fourth solution including gold nanoparticle-attached core-shell nanoparticles may be prepared.

In one embodiment, the functional group may be introduced onto the surface of the ceramic shell, and a plurality of the functional groups may form bonds with a plurality of the gold nanoparticle seeds.

In one embodiment, the functional group may be selected from the group consisting of an amine group (—NH), a thiol group (—SH), a carboxyl group (—COOH), a hydroxyl group (—OH), and dopamine Specifically, the functional group may be an amine group, and the amine group may be introduced onto the surface of the shell by reacting a compound having an amine group with the first core-shell nanoparticles.

In one embodiment, the gold nanoparticle seeds may be bonded to the functional groups so that the gold nanoparticle seeds are attached to the first core-shell nanoparticles.

Here, the gold nanoparticle seeds may be prepared through a preparation method generally used in the art, and specifically, may be synthesized in an aqueous solution using a gold ion precursor solution and a reducing agent.

As the gold ion precursor, one or more selected from the group consisting of gold chloride trihydrate ($HAuCl_4 \cdot 3H_2O$), potassium gold(III) chloride ($K(AuCl_4)$), and potassium dicyanoaurate ($KAu(CN)_2$) may be used, and as the reducing agent, one or more selected from the group consisting of hydroquinone, sodium borohydride ($NaBH_4$), sodium ascorbate, and hydroxylamine may be used.

The reducing agent not only acts as a reducing agent for reducing gold in an aqueous solution but also may impart a negative charge to the periphery of the synthesized gold nanoparticles. Therefore, the gold nanoparticle seeds which have been reduced are well dispersed in the aqueous solution due to having a negative charge on surfaces thereof, and thus are capable of forming a strong bond with the functional groups such as amine groups that they encounter. Accordingly, the gold nanoparticle seeds may form a strong bond with the functional groups on the surface of the ceramic shell of the first core-shell nanoparticles and thereby attached to the first core-shell nanoparticles.

According to the present invention, in the (C) primary growth step, the gold nanoparticles of the gold nanoparticle-attached core-shell nanoparticles are primarily grown.

This step may be carried out by adding a gold ion precursor solution to the fourth solution prepared in the step (B), and thereby a fifth solution may be prepared.

The gold nanoparticle seeds reduced by the reducing agent are too small, and their industrial uses are limited because of their poor optical properties. Therefore, in the present invention, in order to increase the small size of the gold nanoparticle seeds and further improve the optical properties of the same, gold nanoparticles may be grown from the gold nanoparticle seeds attached to the surface of the ceramic shell.

In one embodiment, the step may be carried out by mixing the gold nanoparticle-attached core-shell nanoparticles with a gold ion precursor solution, a reducing agent, and a stabilizer. In addition, in order to inhibit the self-nucleation of the gold ion precursor, the gold ion precursor may be dividedly added. As the gold ion precursor, any of those described above may be used, and as the reducing agent, one or more selected from the group consisting of hydroquinone, sodium borohydride ($NaBH_4$), sodium ascorbate, and hydroxylamine may be used, and as the stabilizer, one or more selected from the group consisting of polyvinylpyrrolidone (PVP) and sodium dodecyl sulfate (SDS) may be used.

In one embodiment, the growth of the gold nanoparticles may be controlled by varying the amount of the gold ion precursor, and the average particle diameter of the grown gold nanoparticles may be in the range of 5 to 50 nm.

In the present invention, since the primary growth is carried out after attaching the gold nanoparticle seeds to the ceramic surface of the first core-shell nanoparticles, the gold nanoparticles grow while being in contact with the ceramic surface and thus are firmly fixed, and this leads to high economic efficiency and easy processing. In addition, as the gold nanoparticles grow, a network of the nanoparticles may be formed, resulting in a solid structure that will never be detached from the ceramic surface.

According to the present invention, in the (D) Raman molecule-functionalized core-shell nanoparticle preparation step, Raman molecule-functionalized core-shell nanoparticles are prepared by functionalizing the primarily grown gold nanoparticles with a Raman molecule.

This step may be carried out by mixing the fifth solution prepared in the step (C) with a Raman molecule solution, and thereby a sixth solution including Raman molecule-functionalized core-shell nanoparticles may be prepared.

In the present invention, since a Raman molecule is used, it is possible to enable cell imaging and biomolecule detection using a SERS phenomenon occurring between the Raman molecule and the second core-shell nanoparticles to be described below. In particular, since a Raman molecule may greatly influence the shape of the shell of the second core-shell nanoparticles, by using a Raman molecule, it is possible to manufacture a composite nanostructure having a desired shape.

The Raman molecule may include one or more selected from the group consisting of 1,4-benzenedithiol (1,4-BDT), fluorescein (FAM), Dabcyl, tetramethyl rhodamine isothiol (TRIT), 7-nitrobenz-2-oxa-1,3-diazol (NBD), Texas Red dye, phthalic acid, terephthalic acid, isophthalic acid, Cresyl Fast Violet, Cresyl Blue Violet, Brilliant Cresyl Blue, para-aminobenzoic acid, erythrosine, biotin, digoxigenin, 5-carboxy-4',5'-dichloro-2',7'-dimethoxy, 5-carboxy-2',4',5',7'-tetrachlorofluorescein, 5-carboxyfluorescein, 5-carboxyrhodamine, 6-carboxyrhodamine, 6-carboxytetramethyl aminophthalocyanine, azomethine, xanthine, succinylfluorescein, aminoacridine, a quantum dot, a carbon nanotube, a carbon allotrope, a cyanide, a thiol, chlorine, bromine, methyl, phosphorus, sulfur, a cyanine dye (Cy3, Cy3.5, or Cy5), and rhodamine. In the Raman molecule solution, the concentration of the Raman molecule may be in the range of 0.01 mM to 1 M. In addition, the solvent of the Raman molecule solution may be an alcohol, water, or a mixture thereof.

According to the present invention, in the (E) secondary growth step, a gold, silver, or gold-silver alloy shell is formed on each of the Raman molecule-functionalized gold nanoparticles of the Raman molecule-functionalized core-shell nanoparticles, and thereby second core-shell nanoparticles may be formed and a magnetic-optical composite nanostructure may be finally manufactured.

This step may be carried out by mixing the sixth solution prepared in the step (D) with a gold ion precursor solution and/or a silver ion precursor solution, and thereby a seventh solution including magnetic-optical composite nanostructures in which a gold, silver, or gold-silver alloy shell has been formed may be prepared. Here, the combination of the gold nanoparticle of the magnetic-optical composite nanostructures and the gold, silver, or gold-silver alloy shell formed on the gold nanoparticle may be referred to as a second core-shell nanoparticle.

In one embodiment, to the sixth solution, a reducing agent, a self-nucleation inhibitor, a stabilizer, and the like may be further added in addition to the gold ion precursor solution and/or the silver ion precursor solution. As the gold ion precursor, the reducing agent, the self-nucleation inhibitor effective for gold, and the stabilizer, any of those described above may be used, and as the silver ion precursor, one or more selected from the group consisting of $AgNO_3$ and $AgClO_4$ may be used. In addition, as a self-nucleation inhibitor effective for silver, acetonitrile may be used.

In one embodiment, the concentration of gold ion in the gold ion precursor solution and the concentration of silver ion in the silver ion precursor solution may be in the range of 0.01 mM to 1 M. In addition, the weight ratio of the gold ion precursor solution and the silver ion precursor solution may be 1:0 to 0:1.

In the present invention, due to the Raman molecule, the result of the secondary growth of gold and/or silver may vary depending on the amounts of the gold ion precursor solution and the silver ion precursor solution.

For example, when only the gold ion precursor solution is used or a mixed solution of the gold ion precursor solution and the silver ion precursor solution in which the amount of gold ions is 50 mol % or more relative to the sum of the amounts of gold ions and silver ions (i.e., ion content (in moles): Au≥Ag) is used, the shell may exhibit an epitaxial growth pattern. That is, a uniform gold or gold-silver alloy shell may be formed. In particular, as the amount of gold ions is increased in the mixed solution, a more epitaxial growth pattern may be exhibited.

On the other hand, when only the silver ion precursor solution is used or a mixed solution of the gold ion precursor solution and the silver ion precursor solution in which the amount of silver ions is greater than 50 mol % relative to the sum of the amounts of gold ions and silver ions (i.e., ion content (in moles): Ag>Au), the shell may grow as crystalline islands, and the islands of a silver shell may locally grow.

When an epitaxial, that is, uniform, gold-silver alloy or gold shell is formed, a network of the gold-silver nanoparticles may be formed (i.e., the plasmon coupling of the gold-silver nanoparticles may occur). Here, when epitaxial growth is exhibited, it means that a uniform thin layer is formed on the gold nanoparticle, and when crystalline islands are exhibited, it means that the shell is formed in a hemispherical shape around the nucleus of the gold nanoparticle. In the present invention, a secondarily grown metal may be referred to as a shell.

In one embodiment, the size of the epitaxially grown second core-shell nanoparticles may be in the range of 5 nm to 100 nm. On the other hand, the size of the second core-shell nanoparticles exhibiting the growth of silver islands may be in the range of 5 nm to 500 nm.

In addition, the present invention relates to a magnetic-optical composite nanostructure manufactured by the above-described method of manufacturing a magnetic-optical composite nanostructure. The magnetic-optical composite nanostructure may be referred to as a composite nanostructure.

The magnetic-optical composite nanostructure of the present invention may include: a first core-shell nanoparticle having a magnetic nanoparticle core and a ceramic shell; and second core-shell nanoparticles, each of which has a gold nanoparticle core and a gold, silver, or gold-silver alloy shell.

In one embodiment, the second core-shell nanoparticle may be bonded to a functional group formed on the surface of the shell of the first core-shell nanoparticle. Here, the second core-shell nanoparticles may be in contact with one another and form a network. Specifically, in the manufacture of the composite nanostructure, the gold nanoparticles bonded to the first core-shell nanoparticle through the functional groups on the shell surface may grow through the primary growth and the secondary growth and form a network.

In addition, the gold nanoparticle core may be functionalized with a Raman molecule.

In one embodiment, the shell of the second core-shell nanoparticle may be in the form of a shell of uniform thickness surrounding the core or the form in which only silver islands have been locally formed on the core.

In addition, the present invention relates to an analyte detection kit, a molecular diagnostic chip, or a diagnostic imaging composition including the above-described magnetic-optical composite nanostructure.

In addition, the present invention relates to a method of detecting, separating, or imaging an analyte, which includes: functionalizing the surface of the above-described magnetic-optical composite nanostructure with a biomolecule capable of binding to an analyte to be detected; exposing the functionalized magnetic-optical composite nanostructure to a sample containing one or more analytes; and identifying an analyte bound to the magnetic-optical composite nanostructure using Raman spectroscopy.

The magnetic-optical composite nanostructure of the present invention is functionalized with a biomolecule capable of recognizing an analyte to be detected and is therefore useful as a probe applicable to detecting various biomolecules.

In one embodiment, the analyte to be detected may be an amino acid, a peptide, a polypeptide, a protein, a glycoprotein, a lipoprotein, a nucleoside, a nucleotide, an oligonucleotide, a nucleic acid, a sugar, a carbohydrate, an oligosaccharide, a polysaccharide, a fatty acid, a lipid, a hormone, a metabolite, a cytokine, a chemokine, a receptor, a neurotransmitter, an antigen, an allergen, an antibody, a substrate, a cofactor, an inhibitor, a drug, a pharmaceutical, a nutrient, a prion, a toxin, a poison, an explosive, a pesticide, a chemical weapon, a biohazard agent, a radioisotope, a vitamin, a heterocyclic aromatic compound, a carcinogen, a mutagen, an anesthetic, an amphetamine, a barbiturate, a hallucinogen, a waste, or a contaminant. When the analyte is a nucleic acid, the analyte may be a nucleic acid such as a gene, viral RNA or DNA, bacterial DNA, fungal DNA, mammalian DNA, cDNA, mRNA, an RNA or DNA fragment, an oligonucleotide, a synthetic oligonucleotide, a modified oligonucleotide, a single- or double-stranded nucleic acid, or a natural or synthetic nucleic acid.

In one embodiment, the biomolecule capable of binding to the surface of the composite nanostructure of the present invention, which is capable of recognizing the analyte, may be an antibody, an antibody fragment, a genetically engineered antibody, a single-chain antibody, a receptor protein, a binding protein, an enzyme, an inhibitor protein, a lectin, a cell adhesion protein, an oligonucleotide, a polynucleotide, a nucleic acid, or an aptamer.

In one embodiment, the Raman spectroscopy may be surface-enhanced Raman spectroscopy (SERS), surface-enhanced resonance Raman spectroscopy (SERRS), or hyper-Raman and/or coherent anti-Stokes Raman spectroscopy (CARS).

The SERS technique fundamentally uses a low-power laser, so it is non-destructive with respect to samples. In addition, since not only a probe manufacturing technique has been developed, but also a material having high biocompatibility is used, the SERS technique is applicable in various ways to the diagnosis of diseases both in vitro and in vivo. In order to increase the mobility and biocompatibility of a probe both in vitro and in vivo, the surface of the probe may be coated with a biocompatible material such as a polymer ligand or silica. In addition, due to using specific reactions (DNA hybridization, antigen-antibody reactions, etc.) occurring between biomaterials, it is possible to diagnose, with high sensitivity, a specific disease both in vitro and in vivo. In addition, the SERS technique may also be used for identifying an individual, confirming kinship, identifying bacteria or cells, or identifying the origins of animals and plants.

Therefore, the non-destructive SERS analysis technique using the composite nanostructure of the present invention is applicable to the real-time monitoring of specific diseases in living cells and in vivo and the development of therapeutic drugs.

Furthermore, since the microstructure of the composite nanostructure of the present invention, which is capable of maximizing a SERS signal, ensures high reproducibility, the composite nanostructure of the present invention is applicable to an ultra-high-sensitivity biomolecule analysis method having very high reliability and is also useful for in-vivo imaging techniques as well as in-vitro diagnostic methods.

In one embodiment, the separation of an analyte may be carried out, for example, by magnetic separation. Since the magnetic-optical composite nanostructure of the present invention has magnetic characteristics, it may be used for easily separating an analyte through magnetic separation.

EXAMPLES

Example 1. Preparation of Magnetic-Optical Composite Nanostructure

1. Synthesis of Iron Oxide (Magnetite ($Fe_3O_4$)) Nanoparticles

The synthesis of iron oxide nanoparticles was carried out through a polyol method.

Iron chloride hexahydrate ($FeCl_3 \cdot 6H_2O$) was used as an iron ion precursor, ethylene glycol (EG) was used as both a reducing agent and a solvent, and sodium acetate (NaOAc) and $H_2O$ were used as auxiliary agents for helping hydrolysis.

2 mmol of $FeCl_3 \cdot 6H_2O$, 6 mmol of NaOAc, and 150 mmol of $H_2O$ were added to 50 mL of EG, input in a 3-neck flask, and then rapidly heated to 200° C. for 15 minutes while mechanically stirring. After maintaining a reaction for 3 hours and 30 minutes, the resultant was cooled and then washed with ethanol.

2. Synthesis of Gold (Au) Nanoparticles

Gold chloride trihydrate ($HAuCl_4 \cdot 3H_2O$) was used as a gold ion precursor, sodium borohydride ($NaBH_4$) was used as a reducing agent, trisodium citrate was used as a stabilizer, and $H_2O$ was used as a solvent.

After adjusting the concentration of each of $HAuCl_4 \cdot 3H_2O$ and trisodium citrate in 50 mL of $H_2O$ to 0.25 mM and then adding 1.5 mL of cold $H_2O$ (including 0.1 M $NaBH_4$), the resultant was reacted at room temperature under continued magnetic stirring. (Preparation of a gold nanoparticle solution)

3. Preparation of Gold Nanoparticle-Attached Core-Shell Nanoparticles

On each of the iron oxide nanoparticles, a silica shell was formed using a Stöber method.

Ethanol and $H_2O$ were used as solvents, PVP was used as a stabilizer, an ammonium hydroxide ($NH_4OH$) solution was used as a catalyst, and TEOS was used as a silica precursor.

After mixing 50 mL of ethanol, 7.5 mL of $H_2O$, 2.5 mL of $NH_4OH$, and 400 mg of PVP, 25 mg of the iron oxide nanoparticles were added to the solution, and thereby a uniformly mixed solution including the iron oxide nanoparticles was obtained. Subsequently, 0.050 mL of TEOS was added to the mixed solution and then shaken at room temperature for 1 hour and 30 minutes. The resultant was washed with ethanol and then dispersed in 10 mL of ethanol. As a result, iron oxide nanoparticle/silica core-shell nanoparticles were obtained. (Preparation of a second solution)

To the iron oxide nanoparticle/silica core-shell nanoparticles, gold nanoparticles were attached.

(3-Aminopropyl)triethoxysilane (APTES) was used as an amine group ($-NH_2$) precursor, and 2-propanol was used as a solvent.

After solvent-substituting 4 ml of the second solution, that is, iron oxide nanoparticle/silica core-shell nanoparticles in ethanol (including iron oxide nanoparticles at 2.5 mg/ml), with 10 mL of 2-propanol, 0.050 mL of APTES was added and then shaken. Subsequently, after sonicating at 80° C. for four hours, the resultant was washed with $H_2O$ and then dispersed in 5 mL of $H_2O$. (Preparation of a third solution)

5 mL of the third solution including the iron oxide nanoparticle/silica core-shell nanoparticle whose surface is functionalized with an amine group was mixed with 30 ml of the gold nanoparticle solution prepared in "2. Synthesis of gold (Au) nanoparticles" and shaken for 16 hours. Then, as the post-treatment, $H_2O$ in which 1 wt % of PVP is dissolved was added as a stabilizer and uniformly shaken. Subsequently, the resultant was washed with $H_2O$ and then dispersed in 20 mL of $H_2O$. (Preparation of a fourth solution)

4. Preparation of Magnetic-Optical Composite Nanostructure

In order to primarily grow the gold particles on the iron oxide nanoparticle/silica core-shell nanoparticles, PVP was used as a stabilizer, $HAuCl_4·3H_2O$ was used as a gold ion precursor, L-ascorbic acid was used as a reducing agent, and $H_2O$ was used as a solvent.

A 5 mM $HAuCl_4·3H_2O$ solution in $H_2O$ was prepared. 0.4 mL of the fourth solution, which is a solution of gold nanoparticle-attached core-shell nanoparticles (including iron oxide nanoparticles at 0.5 mg/ml), 3.6 mL of $H_2O$ (including PVP at 1 wt %), and 0.080 mL of a 20 mM aqueous ascorbic acid solution were mixed and uniformly shaken. Subsequently, the 5 mM $HAuCl_4·3H_2O$ solution was added in six portions of 0.02 mL every 10 minutes to inhibit self-nucleation. Then, the mixture was reacted for one hour while shaking at room temperature. The resultant was washed with $H_2O$ and then dispersed in 4 mL of $H_2O$. (Preparation of a fifth solution)

Subsequently, functionalization with a Raman molecule was carried out using 1,4-benzenedithiol (1,4-BDT).

The fifth solution, which is a solution including the core-shell nanoparticles to which the primarily grown gold nanoparticles are attached, was added to 0.040 mL of a 1 mM 1,4-BDT solution in ethanol and reacted for 1 hour and 30 minutes at room temperature under continued stirring. The resultant was washed with $H_2O$ and then dispersed in 0.4 mL of $H_2O$. (Preparation of a sixth solution)

On the gold nanoparticles which had been primarily grown and then functionalized with a Raman molecule, a shell made of gold and silver was secondarily grown.

In order to achieve the secondary growth by growing the shell, PVP was used as a stabilizer, AgCl was used as a formation inhibitor, ascorbic acid was used as a reducing agent, acetonitrile was used as a self-nucleation inhibitor effective for silver (Ag), $HAuCl_4·3H_2O$ was used as a gold ion precursor, and $AgNO_3$ was used as a silver ion precursor.

That is, to a solution of the gold nanoparticles which had been primarily grown and then functionalized with a Raman molecule (sixth solution), 3.6 mL of $H_2O$ (including PVP at 1 wt %) and 0.080 mL of a 20 mM aqueous ascorbic acid solution were mixed and uniformly shaken. Subsequently, a 5 mM aqueous $HAuCl_4·3H_2O$ solution and a 5 mM aqueous $AgNO_3$ solution were prepared. By mixing the aqueous solutions at a ratio of 1:0 (S1), 2:1 (S2), 1:1 (S3), 1:2 (S4), or 0:1 (S5) while constantly maintaining the sum of the aqueous solutions at 0.08 mL, a mixed aqueous solution was prepared. The mixed aqueous solution was added in four portions of 0.02 mL every 10 minutes. After reacting for 40 minutes at room temperature while shaking, the resultant was washed with $H_2O$ and then dispersed in 4 mL of $H_2O$. (Preparation of a seventh solution)

Comparative Example 1

Magnetic-optical composite nanostructures were manufactured in the same manner as in Example 1 except that functionalization with a Raman molecule was not performed.

Experimental Example 1. Physical Properties of Magnetic-Optical Composite Nanostructure FIG. 1 is a set of images including (a) a schematic diagram illustrating a process (steps) of manufacturing a magnetic-optical composite nanostructure according to the present invention, (b) TEM images obtained in each step of the schematic diagram of (a), and (c) a TEM image and EDX images of S3 showing Fe, Si, Au, S (present as a thiol group (—SH) in a Raman molecule), and Ag.

Referring to FIG. 1, it can be seen that each of the magnetic-optical composite nanostructures of the present invention includes: a first core-shell nanoparticle having a magnetic nanoparticle core and a silica shell; and second core-shell nanoparticles having a gold nanoparticle core and a gold-silver alloy shell, and the second core-shell nanoparticles are bonded to the functional groups formed on the surface of the shell of the first core-shell nanoparticle.

Figure 2:
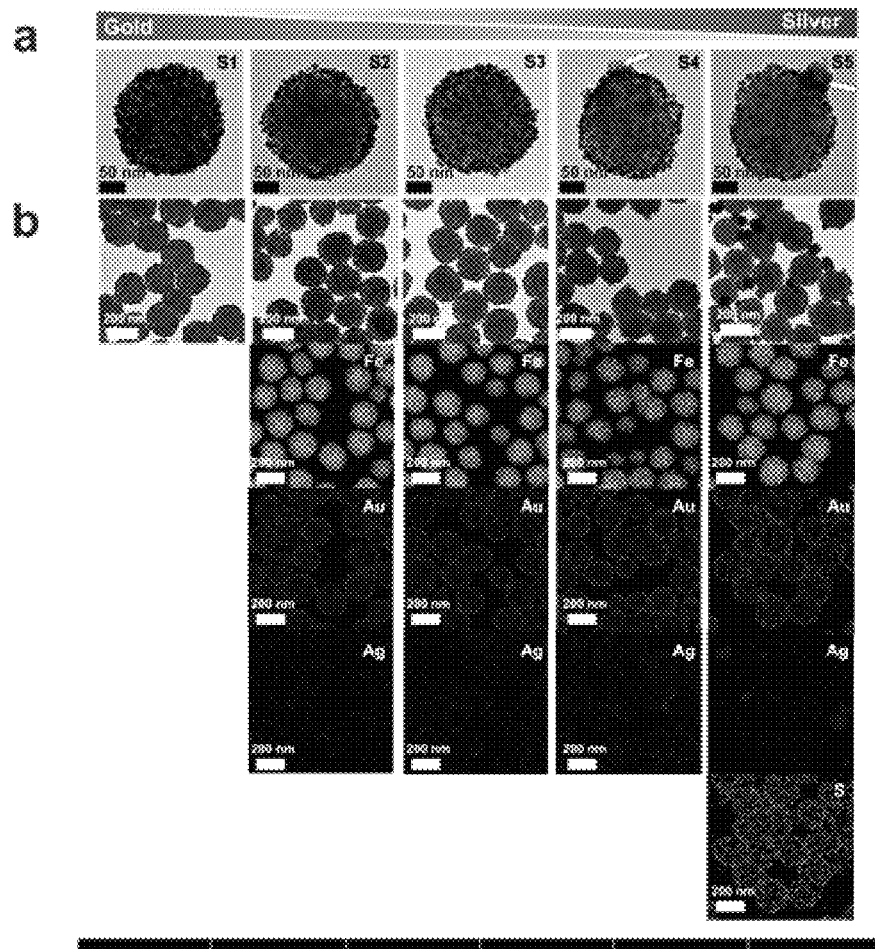
FIG. 2 is a set of images including (a) TEM images of composite nanostructures manufactured with different ratios of a gold ion precursor and a silver ion precursor, (b) low-magnification TEM images and EDX images of the same composite nanostructures, and a table showing gold/silver atomic percentages in the same composite nanostructures, and (c) schematic diagrams illustrating the principles of composite nanostructure synthesis.
Figure 2:
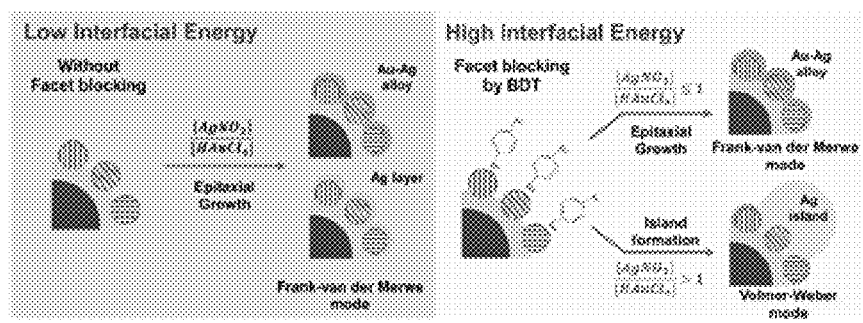

In addition, FIG. 2 is a set of images including (a) TEM images of composite nanostructures manufactured with different ratios of a gold ion precursor and a silver ion precursor, (b) low-magnification TEM images and EDX images of the same composite nanostructures and a table showing gold/silver atomic percentages in the same composite nanostructures, and (c) schematic diagrams illustrating the principles of composite nanostructure synthesis.

Referring to FIG. 2, it can be seen that during the secondary growth, whereas the gold ions formed a uniform shell, the silver ions only formed silver islands locally, thereby resulting in a dumbbell-like structure.

Figure 3:
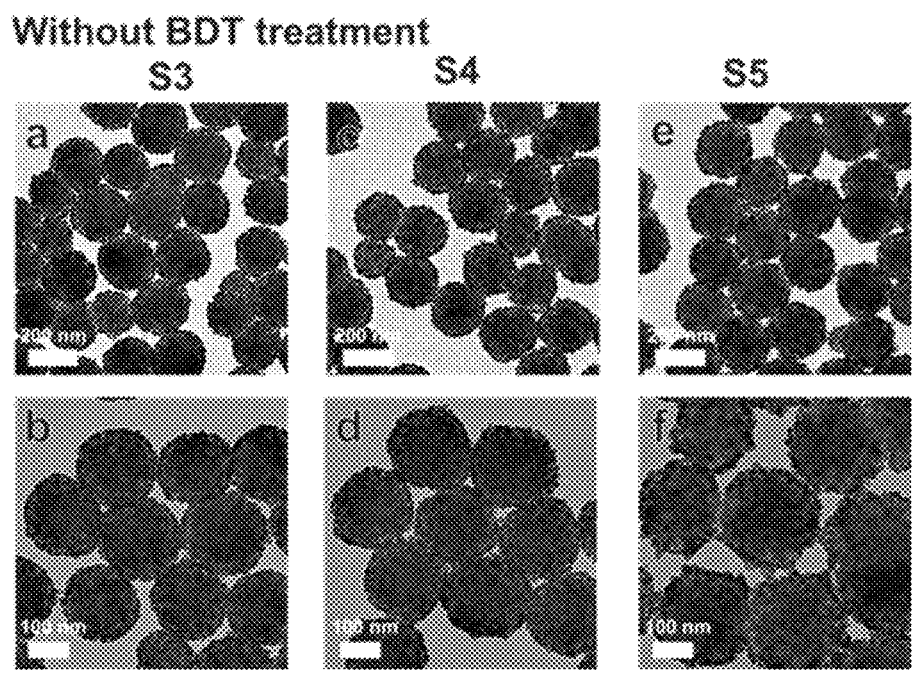
FIG. 3 is a set of TEM images showing that when primarily grown gold nanoparticles are subjected to secondary growth without being functionalized with 1,4-BDT, a uniform, secondarily grown gold/silver shell is formed.

It can be seen that in the case of Comparative Example 1 where a Raman molecule was not used, all the prepared nanoparticles grew while forming a uniform shell (see FIG. 3). Based on this observation, it can be seen that the Raman molecule helps to control the secondary growth by the gold and/or silver ions and thereby a composite nanostructure having a desired shape is produced.

Figure 4:
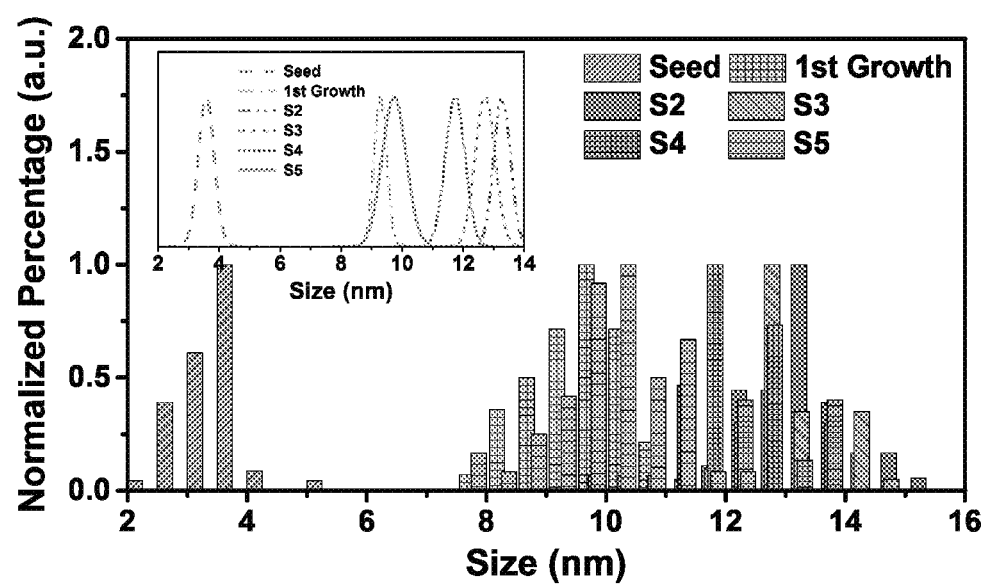
FIG. 4 shows a particle size distribution in TEM images of second core-shell nanoparticles attached to first core-shell nanoparticles, wherein, when measuring the particle size distribution, the size of all particles except those in islands is measured.

In addition, FIG. 4 shows a particle size distribution in TEM images of second core-shell nanoparticles.

Referring to FIG. 4, it can be seen that the average particle diameter of the gold nanoparticle seeds increases through the primary growth and the secondary growth.

Figure 5:
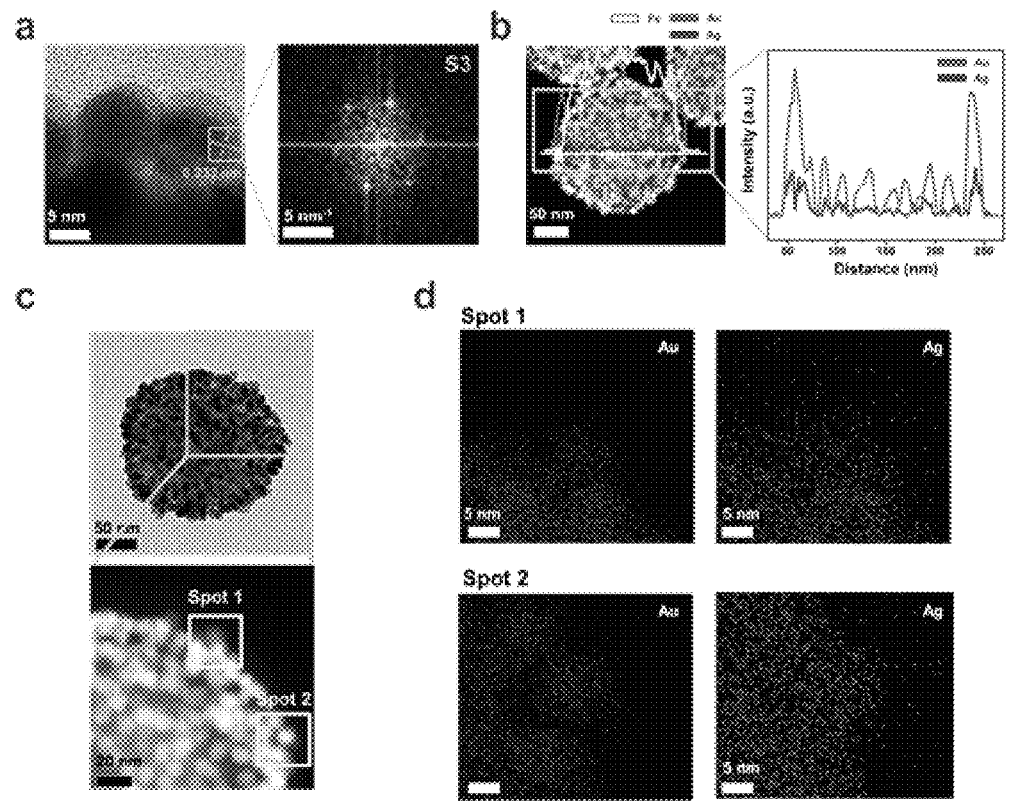
FIG. 5 is a set of images including (a) a high-resolution TEM image and a fast Fourier transform (FFT) diffraction image showing epitaxial secondary gold/silver growth, (b) an EDX image of a magnetic-optical composite nanostructure and the result of measuring the content ratio of gold and silver atoms in second core-shell nanoparticles, (c) high-magnification TEM images of a magnetic-optical composite nanostructure, and (d) EDX results showing the composition of second core-shell nanoparticles (gold/silver nanoparticles) densely packed on a first core-shell nanoparticle.

In addition, FIG. 5 is a set of images illustrating S3, which include (a) a TEM image and an FFT diffraction image showing the secondary gold/silver growth, (b) an EDX image and the result of measuring the contents of gold and silver atoms in a second core-shell nanoparticle, (c) high-magnification TEM images of the magnetic-optical composite nanostructure, and (d) EDX results showing the composition of second core-shell nanoparticles (gold/silver nanoparticles) densely packed on a first core-shell nanoparticle.

Referring to FIG. 5, it can be seen that the magnetic-optical composite nanostructure has a structure in which second core-shell nanoparticles are densely packed on the surface of a first core-shell nanoparticle. Also, in the composite nanostructure S3, the shell portion of the second core-shell nanoparticles appears to be a gold-silver alloy.

Figure 6:
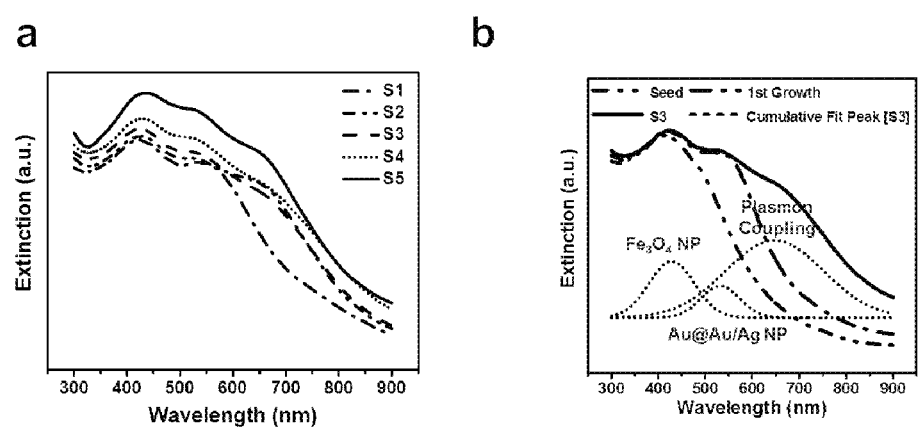
FIG. 6 shows (a) the result of evaluating optical properties according to the ratio of a gold ion precursor and a silver ion precursor using a UV-Vis spectrometer and (b) the result of evaluating the change in optical properties according to the primary gold growth and the secondary gold/silver growth using a UV-Vis spectrometer.

In addition, FIG. 6 shows (a) the result of evaluating optical properties according to the ratio of a gold ion precursor and a silver ion precursor using a UV-Vis spectrometer and (b) the result of evaluating the change in optical properties according to the primary gold growth and the secondary gold/silver growth using a UV-Vis spectrometer.

Referring to FIG. 6, it can be seen that structure-specific optical properties are exhibited due to the densely packed second core-shell nanoparticles (gold/silver nanoparticles).

In addition, FIG. 7A shows high-magnification TEM images which confirm the fact that when the mixing ratio of the gold precursor (5 mM $HAuCl_4·3H_2O$) and the silver precursor (5 mM $AgNO_3$) in the secondary gold/silver growth is 1:1 (S3), as the amount of the mixed aqueous solution increases, the thickness of the gold-silver alloy shell increases. Here, the mixed aqueous solution was added in 3 (a1), 8 (a2), and 16 (a3) portions of 0.02 mL. In addition, FIG. 7B shows the result of evaluating, using a UV-Vis spectrometer, the change in optical properties according to the thickness of a gold-silver alloy shell formed in the secondary gold/silver growth.

Figure 7:
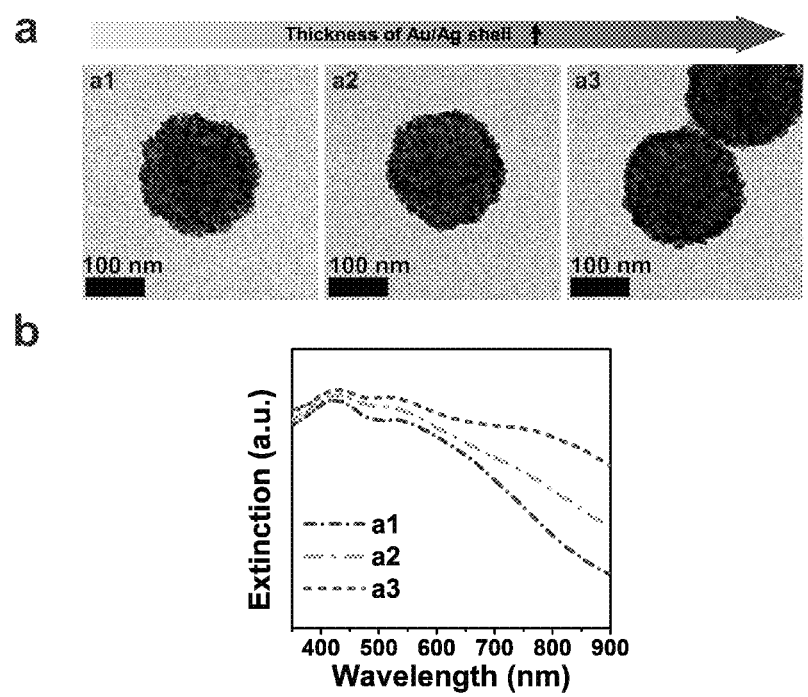
FIG. 7 shows (a) TEM images illustrating the change in the size of second core-shell nanoparticles (gold/silver nanoparticles) densely packed in a magnetic-optical composite nanostructure according to the amounts of gold and silver ion precursors added in the secondary gold/silver growth stage when the ratio of the gold ion precursor and the silver ion precursor is fixed at 1:1 (S3) and (b) the result of evaluating the change in optical properties using a UV-Vis spectrometer.

As shown in FIG. 7, as the size of the second core-shell nanoparticles (gold/silver nanoparticles) increases, the light absorption intensity in the infrared wavelength region gets stronger, and this is because the second core-shell nanoparticles bonded to the first core-shell nanoparticles are not only bigger but also closer to one another. Based on this result, it can be seen that by adjusting the usage amounts of the gold precursor and the silver precursor, it is possible to control the size and optical properties of the second core-shell nanoparticles.

Experimental Example 2. Cancer Cell Imaging Using Magnetic-Optical Composite Nanostructure The magnetic-optical composite nanostructures manufactured in Examples were placed on a cover glass and dried, and the intensity of a SERS signal generated from a single nanostructure was measured by confocal Raman microscopy. For this, a 100× objective lens and lasers having a wavelength of 633 nm and 785 nm were used. The laser having a wavelength of 633 nm was irradiated with a laser power of 1 mW, and the measurement was carried out with an acquisition time of one second. The laser having a wavelength of 785 nm was irradiated with a laser power of 4 mW, and the measurement was carried out with an acquisition time of five seconds.

Figure 8:
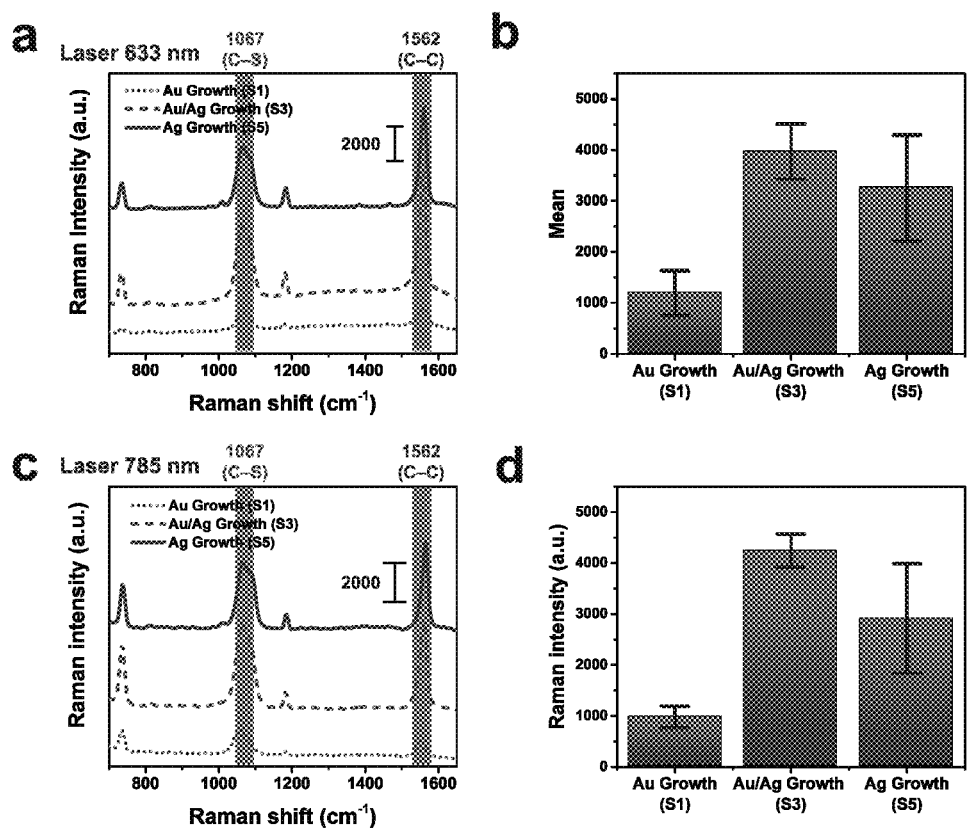
FIG. 8 shows (a) the result of measuring the intensity of SERS signals generated, at a laser wavelength of 633 nm, from composite nanostructures manufactured using different ratios of a gold ion precursor and a silver ion precursor for the secondary growth, (b) the result of evaluating signal reliability by measuring SERS signal intensity at 1067 cm$^{-1}$ corresponding to one of the fingerprint peaks of 1,4-BDT seven times, (c) the result of measuring the intensity of SERS signals generated, at a laser wavelength of 785 nm, from composite nanostructures manufactured using different ratios of a gold ion precursor and a silver ion precursor for the secondary growth, and (d) the result of evaluating signal reliability by measuring SERS signal intensity at 1067 cm$^{-1}$ corresponding to one of the fingerprint peaks of 1,4-BDT seven times.

FIG. 8A shows the result of measuring the intensity of SERS signals generated, at a laser wavelength of 633 nm, from composite nanostructures having different ratios of a gold ion precursor and a silver ion precursor for the secondary growth. The SERS signals were detected at 735 $cm^{-1}$, 1067 $cm^{-1}$, and 1562 $cm^{-1}$ corresponding to the fingerprint peaks of 1,4-BDT.

FIG. 8B shows the result of evaluating signal reliability by measuring SERS signal intensity at 1067 $cm^{-1}$ corresponding to one of the fingerprint peaks of 1,4-BDT shown in FIG. 8A seven times.

FIG. 8C shows the result of measuring the intensity of SERS signals generated, at a laser wavelength of 785 nm, from composite nanostructures having different ratios of a gold ion precursor and a silver ion precursor for the secondary growth. The SERS signals were detected at 735 $cm^{-1}$, 1067 $cm^{-1}$, and 1562 $cm^{-1}$ corresponding to the fingerprint peaks of 1,4-BDT.

FIG. 8D shows the result of evaluating signal reliability by measuring SERS signal intensity at 1067 $cm^{-1}$ corresponding to one of the fingerprint peaks of 1,4-BDT shown in FIG. 8C seven times.

Based on the above results, it can be seen that the composite nanostructures S1 and S3 form a uniform shell, and the SERS signal intensity increases as the silver content increases. On the other hand, in the case of the composite nanostructure S5, although the silver content is the highest, a SERS signal with a lower intensity than S3 is measured, and this is because silver islands are formed locally, resulting in a shell with a dumbbell-like structure.

Meanwhile, to functionalize the surface of the composite nanostructure S3 with a carboxyl group, SH-PEG-COOH (molecular weight (Mw): 5000), $H_2O$ as a solvent, and SDS as a stabilizer were used.

1 mL of a composite nanostructure solution (0.01% SDS; including iron oxide nanoparticles at 0.05 mg/mL), which is the seventh solution, and 0.2 mL of 5 mg/mL SH-PEG-COOH were uniformly mixed, shaken for 16 hours, and washed with $H_2O$ and then dispersed in 1 mL of $H_2O$. (Preparation of a carboxyl group-functionalized composite nanostructure solution) Subsequently, the solution was functionalized with cyclo(-RGDyK), which is a peptide used for cell imaging Specifically, 1 mL of the carboxyl group-functionalized composite nanostructure solution was solvent-substituted with 1 mL of a 50 mM MES buffer. 0.1 mL of a 1-ethyl-3-(3-dimethylaminopropyl) carbodiimide hydrochloride (EDC) solution (20 mM) and 0.1 mL of a sulfo-N-hydroxysulfosuccinimide (NHS) solution (20 mM) were added, shaken for at least 10 minutes, and washed with $H_2O$ and then dispersed in 0.2 mL of $H_2O$. Subsequently, 0.2 mL of an aqueous cyclo(-RGDyK) solution (1 mM) was added and then stirred for at least six hours, and the resultant was washed with $H_2O$ or phosphate buffer saline (PBS) and then dispersed in 0.5 mL of a solution.
(Preparation of a Cyclo(-RGDyK)-Functionalized Composite Nanostructure Solution)

70,000 of each of HeLa cells, U87MG cells, and MCF7 cells were attached to a glass bottom dish and incubated in 0.025 mL of the cyclo(-RGDyK)-functionalized composite nanostructure solution for at least three hours and fixed. Subsequently, cell imaging was performed through confocal Raman microscopy. Here, for the HeLa cells, a laser having a wavelength of 785 nm was irradiated with a laser power of 4.36 mW, and the measurement was carried out with an acquisition time of 0.05 seconds. For the U87MG cells and the MCF7 cells, a laser having a wavelength of 633 nm was irradiated with a laser power of 3.9 mW, and the measurement was carried out with an acquisition time of 0.035 seconds.

Figure 9:
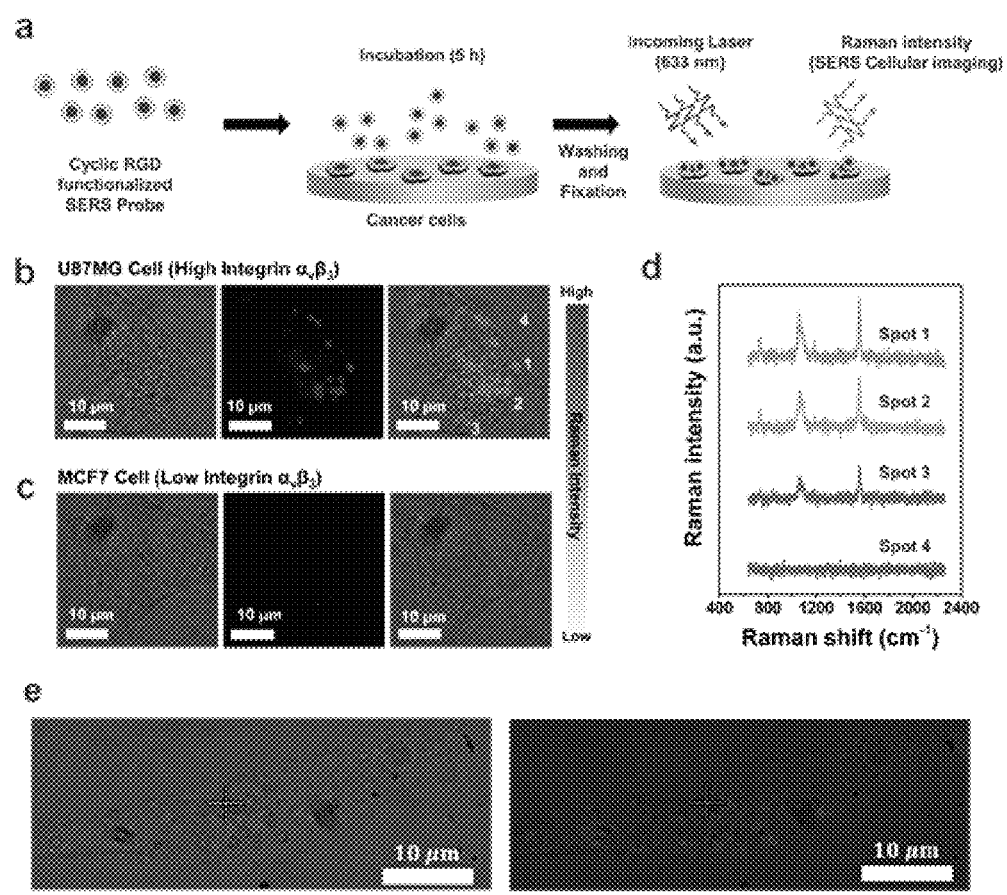
FIG. 9 shows the result of U87MG, MCF7, and HeLa cell imaging performed using composite nanostructures (S3)

FIG. 9 shows U87MG, MCF7, and HeLa cancer cell imaging results.

Referring to FIG. 9, it can be seen that the magnetic-optical composite nanostructure is useful as a cell imaging probe in an aqueous solution.

Specifically, FIG. 9A is a schematic diagram illustrating the application of the magnetic-optical composite nanostructure as a cancer cell imaging probe. In this exemplary embodiment, cells were incubated in the presence of composite nanostructures whose surface is functionalized with cyclo(-RGDyK), washed, fixed, and imaged by being irradiated with a laser.

FIG. 9B shows the result of imaging the U87MG cells which express a high level of integrin αvβ3. Due to a receptor of cyclo(-RGDyK) that specifically binds to integrin αvβ3, the composite nanostructure enables cancer cell imaging. In the images, the red dots indicate the sites where the composite nanostructures are present, and it can be seen in the images that a significant number of the composite nanostructures are attached to the surface of the cells.

FIG. 9C shows the result of imaging the MCF7 cells which express a low level of integrin αvβ3. These cancer cells can be imaged using the composite nanostructure. The red dots indicate the sites where the composite nanostructures are present, and it can be seen in the images that the composite nanostructures are not attached to the surface of the cells.

FIG. 9D shows the SERS signal intensity at specific regions of U87MG cancer cells imaged using the composite nanostructures attached to the surface of the cells. It can be seen that no SERS signal generated by the composite nanostructures is detected in the parts not corresponding to the cells, and a SERS signal with high intensity is generated at the surface of the cells by the composite nanostructures.

In addition, FIG. 9E shows the result of HeLa cell imaging. Specifically, FIG. 9E shows the result of imaging the cancer cells using the composite nanostructures including a receptor of cyclo(-RGDyK) that specifically binds to integrin $\alpha v \beta 3$. The red dots indicate the sites where the composite nanostructures are present, and it can be seen that a significant number of the composite nanostructures are attached to the surface of the cells.

Based on the results illustrated in FIG. 9, it can be seen that the composite nanostructure is applicable to various cancer cells. In addition, it can be seen that the composite nanostructure is applicable at various laser wavelengths (633 nm and 785 nm). In particular, it can be seen that the composite nanostructure of the present invention has excellent dispersibility in an aqueous solution and is useful as a cell imaging probe.

Experimental Example 3. Cancer Cell Separation Using Magnetic-Optical Composite Nanostructure A PBS solution in which 130,000 U87MG cells had been dispersed was mixed with 0.05 mL of the cyclo(-RGDyK)-functionalized composite nanostructure solution prepared in Experimental Example 2 and incubated for 30 minutes, and the resultant was washed in a PBS solution using magnetic separation and then re-dispersed in 1 mL of a PBS solution.

Subsequently, the magnetically separated cancer cells were injected into a microfluidic chip channel. After placing a magnet on one side of the microfluidic chip channel so that the cancer cells were captured in a specific direction, the cancer cells were imaged by being irradiated with a 785-nm laser.

Figure 10:
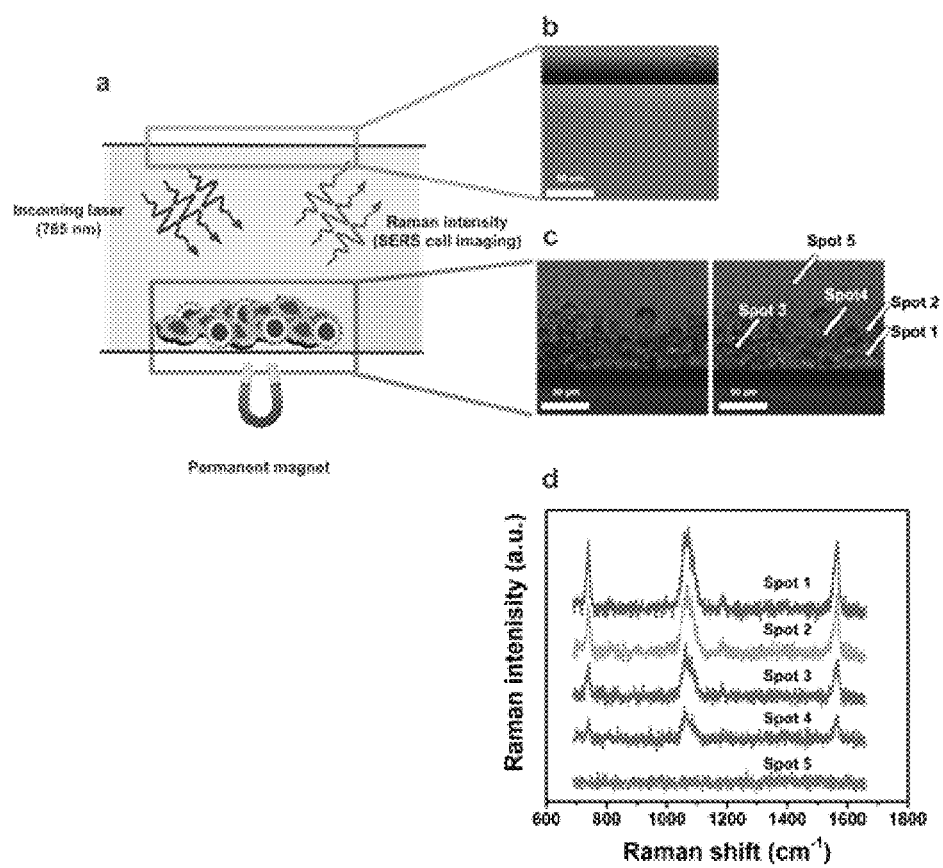
FIG. 10 shows the result of the magnetic separation and imaging of U87MG cells performed using composite nanostructures in which the ratio of a gold ion precursor and a silver ion precursor is 1:1, that is, S3.

FIG. 10 shows the result of the magnetic separation and imaging of U87MG cells.

Referring to FIG. 10, it can be seen that the magnetic-optical composite nanostructure is suitable for use as a probe for cell separation and imaging.

Specifically, FIG. 10A is a schematic diagram illustrating the cell separation and imaging performed using the magnetic-optical composite nanostructure. FIG. 10B is a confocal Raman micrograph showing the side of the microfluidic channel on which a magnet is not placed, and FIG. 10C shows a confocal Raman micrograph and an imaging result showing the side of the microfluidic channel on which a magnet is placed. FIG. 10D shows the result of measuring a SERS signal generated, using a 785-nm laser, in the regions labeled in the image of the magnetically captured cancer cells shown in FIG. 10c.

Referring to FIG. 10, it can be confirmed that the composite nanostructure is applicable to the magnetic separation and imaging of cancer cells. In addition, it can be seen that the composite nanostructure is applicable at various laser wavelengths (633 nm and 785 nm). In particular, it can be seen that the composite nanostructure of the present invention has excellent dispersibility in an aqueous solution and is suitable for use as a probe for both cell imaging and magnetic separation.

Experimental Example 4. Cancer Cell Collection Using Magnetic-Optical Composite Nanostructure A PBS solution including 130,000 U87MG cells was mixed with 0.050 mL of the cyclo(-RGDyK)-functionalized composite nanostructure solution prepared in Experimental Example 2 and incubated for 30 minutes, and the resultant was washed in a PBS solution using magnetic separation and then re-dispersed in 1 mL of a PBS solution, and the number of the magnetically separated cells was counted.

Figure 11:
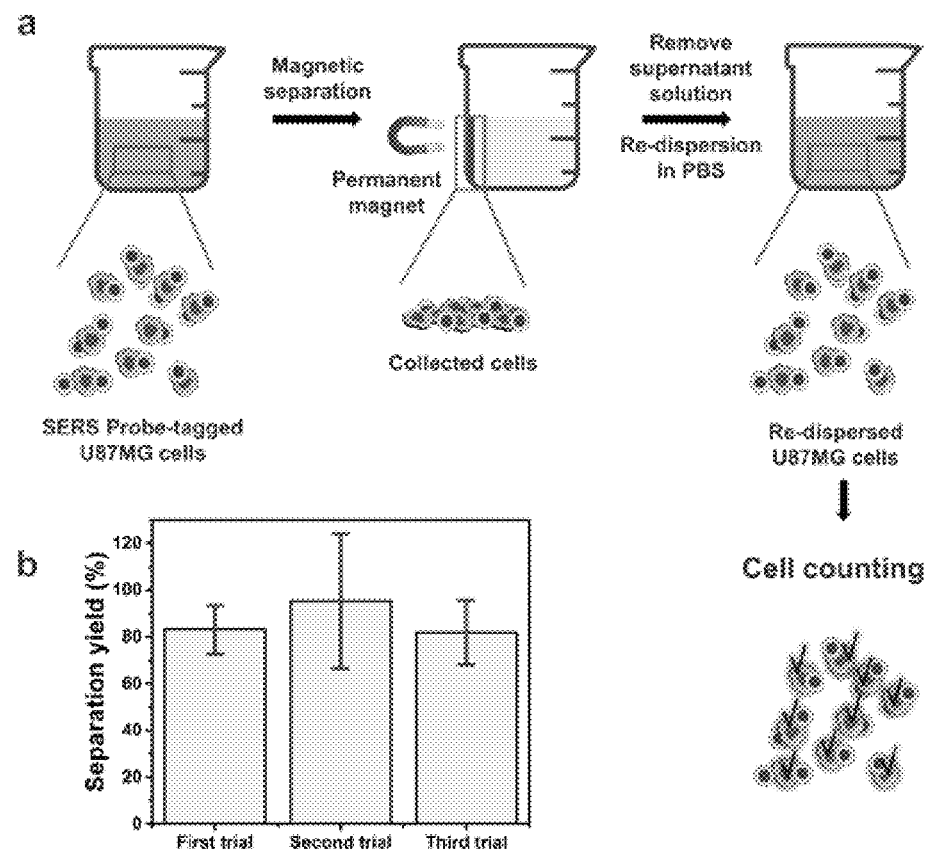
FIG. 11 shows the result of evaluating the efficiency of magnetic separation of U87MG cells performed using composite nanostructures in which the ratio of a gold ion precursor and a silver ion precursor is 1:1, that is, S3.

FIG. 11 shows the result of evaluating the efficiency of magnetic separation of U87MG cells.

Referring to FIG. 11, it can be quantitatively confirmed that the magnetic-optical composite nanostructure is suitable for use in cell collection.

Specifically, FIG. 11A is a schematic diagram illustrating the evaluation of the efficiency of cell separation performed using the magnetic-optical composite nanostructure. FIG. 11B shows the cell separation efficiency.

Based on the results illustrated in FIG. 11, it can be confirmed that the composite nanostructure is applicable as a probe for the magnetic separation of cancer cells.

Experimental Example 5. Immunity Detection Using Magnetic-Optical Composite Nanostructure In order to functionalize the surface of the composite nanostructure S3 with a carboxyl group, SH-PEG-COOH (molecular weight (Mw): 5,000), $H_2O$ as a solvent, and SDS as a stabilizer were used.

1 mL of a composite nanostructure solution (0.01% SDS), which is the seventh solution, and 0.2 mL of 5 mg/mL SH-PEG-COOH were uniformly mixed, shaken for 16 hours, and washed with $H_2O$ and then dispersed in 1 mL of $H_2O$ (0.2 mg/mL).

Subsequently, the resultant was functionalized with an antibody capable of detecting influenza A, which is used to detect influenza A immunity. Specifically, 1 mL of the carboxyl group-functionalized composite nanostructure solution was solvent-substituted with 1 mL of an MES buffer (50 mM). 0.1 mL of an EDC solution (20 mM) and 0.1 mL of an NHS solution (20 mM) were added, shaken for at least 10 minutes, and washed with $H_2O$ and then dispersed in 0.2 mL of $H_2O$. Subsequently, 0.1 mL of a PBS-based solution (0.5 mg/mL) including the antibody capable of detecting a specific antigen was added and then stirred for at least 16 hours, and the resultant was washed with PBS and then dispersed in 0.5 mL of a PBS solution (0.4 mg/mL).

A substrate for antibody-antigen sandwich binding was prepared by functionalizing an Au substrate with an antibody capable of capturing a specific antigen. Specifically, a 4 mm×4 mm Au substrate was input in 0.1 mL of an aqueous 3-mercaptopropionic acid solution (10 mM) and $H_2O$ and shaken for at least 12 hours. Subsequently, after solvent substituting with 1 mL of an MES buffer (50 mM), 0.1 mL of an EDC solution (20 mM) and 0.1 mL of an NHS solution (20 mM) were added, shaken for at least 20 minutes, and washed with PBS. 1 mL of a PBS solution and 0.1 mL of a solution (0.05 mg/mL) including an antibody capable of capturing influenza A were added and shaken for at least 12 hours at room temperature. Subsequently, the resultant was stored in 1 mL of a 1% bovine serum albumin solution in PBS.

After magnetically separating a specific antigen by shaking the same with the composite nanostructures functionalized with the influenza A detection antibody, the resultant was reacted with the Au substrate functionalized with an antibody capable of capturing the specific antigen, and then washed with a PBS solution including Tween 20. After drying, the resultant was observed using a 100× objective lens, and by using a laser having a wavelength of 785 nm, the SERS signal intensity per 25 µm² area at different antigen concentrations was measured. Here, the acquisition time was one second per 1 µm² area.

FIG. 12A shows scanning electron micrographs illustrating the cases in which the composite nanostructure whose surface is functionalized with an antibody capable of detecting influenza A virus and the Au substrate functionalized with an antibody capable of capturing influenza A virus were used at different influenza A antigen concentrations. FIG. 12B shows the SERS signal intensity per 25 µm² area according to an influenza A antigen concentration.

Figure 12:
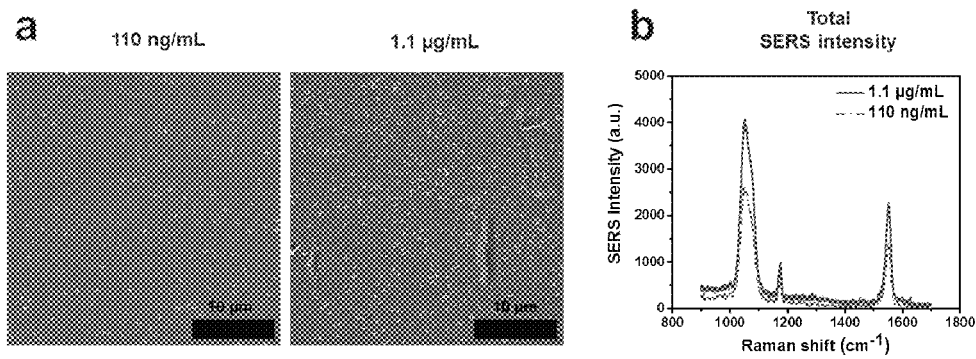
FIG. 12 is a set of images including (a) scanning electron micrographs illustrating the cases in which the composite nanostructures (S3) whose surface is functionalized with an antibody capable of detecting influenza A virus and a gold (Au) substrate functionalized with an antibody capable of capturing influenza A virus were used at different influenza A antigen concentrations, and illustrating (b) the SERS signal intensity per 25 μm$^2$ area according to an influenza A antigen concentration.

Referring to FIG. 12, it can be seen that the higher the concentration of the influenza A antigen, the more detection antibody-functionalized composite nanostructures are bound to the Au substrate. In addition, it can be seen that the higher the concentration of the antigen, the higher the intensity of the SERS signal is obtained from a given area of the Au substrate.

Based on the above results, it can be confirmed that the composite nanostructure of the present invention is applicable in various fields of the diagnostic market, such as the diagnosis of disease, biochips, and the like.

The present invention provides a method of manufacturing multifunctional nanoparticles of various structures by chemically bonding precious metal nanoparticle seeds to the surface of a magnetic nanoparticle and growing the precious metal nanoparticle seeds.

In the present invention, it is possible to manufacture various types of magnetic-optical composite nanostructures by adjusting the content ratio of a gold ion precursor and a silver ion precursor.

Due to being functionalized with a Raman molecule and a biocompatible organic molecule, the magnetic-optical composite nanostructure of the present invention can specifically capture, detect, or separate a biomolecule or biomaterial and enable cell imaging.

Therefore, the composite nanostructure of the present invention can be utilized in various biomedical fields such as the diagnosis of disease, cell separation, and imaging.

What is claimed is:

1. A method of manufacturing a magnetic-optical composite nanostructure, comprising:
    preparing a first core-shell nanoparticle by forming a ceramic shell on a magnetic nanoparticle;
    preparing a gold nanoparticle-attached core-shell nanoparticle by attaching gold nanoparticles to the first core-shell nanoparticle;
    primarily growing the gold nanoparticles of the gold nanoparticle-attached core-shell nanoparticle;
    preparing a Raman molecule-functionalized core-shell nanoparticle by functionalizing the primarily grown gold nanoparticles with a Raman molecule; and
    preparing second core-shell nanoparticles by forming a gold, silver, or gold-silver alloy shell on each of the Raman molecule-functionalized gold nanoparticles of the Raman molecule-functionalized core-shell nanoparticle,
    wherein in the forming of the gold, silver, or gold-silver alloy shell, the concentration of gold ions in a gold ion precursor solution and the concentration of silver ions in a silver ion precursor solution are in the range of 0.01 mM to 1 M, and the weight ratio of the gold ion precursor solution and the silver ion precursor solution is 1:0 to 0:1.

2. The method of claim 1, wherein the magnetic nanoparticle is a metal oxide nanoparticle, and the metal oxide is one or more selected from the group consisting of FeO, $Fe_2O_3$, $Fe_3O_4$, $CoFe_2O_4$, $NiFe_2O_4$, $MnFe_2O_4$, $TiO_2$, $ZrO_2$, $CeO_2$, $Al_2O_3$, and MgO.

3. The method of claim 1, wherein the magnetic nanoparticle has an average particle diameter of 10 to 500 nm.

4. The method of claim 1, wherein the ceramic includes one or more selected from the group consisting of silica, titania, zirconia, alumina, and zeolite.

5. The method of claim 1, wherein the preparing the gold nanoparticle-attached core-shell nanoparticle includes:
    introducing a functional group onto a surface of the shell of the first core-shell nanoparticles; and
    allowing a gold nanoparticle seed to be bonded to the functional group.

6. The method of claim 5, wherein the functional group includes one or more selected from the group consisting of an amine group (—NH), a thiol group (—SH), a carboxyl group (—COOH), a hydroxyl group (—OH), and dopamine.

7. The method of claim 1, wherein, in the primarily growing the gold nanoparticles, the grown gold nanoparticles have an average particle diameter of 5 to 50 nm.

8. The method of claim 1, wherein in the preparing the Raman molecule-functionalized core-shell nanoparticle, the Raman molecule includes one or more selected from the group consisting of 1,4-benzenedithiol (BDT), fluorescein (FAM), Dabcyl, tetramethyl rhodamine isothiol (TRIT), 7-nitrobenz-2-oxa-1,3-diazol (NBD), Texas Red dye, phthalic acid, terephthalic acid, isophthalic acid, Cresyl Fast Violet, Cresyl Blue Violet, Brilliant Cresyl Blue, para-aminobenzoic acid, erythrosine, biotin, digoxigenin, 5-carboxy-4',5'-dichloro-2',7'-dimethoxy, 5-carboxy-2',4',5',7'-tetrachlorofluorescein, 5-carboxyfluorescein, 5-carboxyrhodamine, 6-carboxyrhodamine, 6-carboxytetramethyl aminophthalocyanine, azomethine, xanthine, succinylfluorescein, aminoacridine, a quantum dot, a carbon nanotube, a carbon allotrope, a cyanide, a thiol, chlorine, bromine, methyl, phosphorus, sulfur, a cyanine dye (Cy3, Cy3.5, or Cy5), and rhodamine.

9. The method of claim 1, wherein, when only the gold ion precursor solution is used or a mixed solution of the gold ion precursor solution and the silver ion precursor solution in which the amount of the gold ions is 50 mol % or more relative to the sum of the amounts of the gold ions and the silver ions is used, the shell exhibits an epitaxial growth pattern.

10. The method of claim 9, wherein the size of the epitaxially grown second core-shell nanoparticle is in the range of 5 nm to 100 nm.

11. The method of claim 1, wherein, when only the silver ion precursor solution is used or a mixed solution of the gold ion precursor solution and the silver ion precursor solution in which the amount of the silver ions is more than 50 mol % relative to the sum of the amounts of the gold ions and the silver ions is used, the shell grows as a crystalline island.

12. The method of claim 11, wherein the size of the second core-shell nanoparticle exhibiting the growth of a silver island is in the range of 5 nm to 500 nm.

* * * * *